United States Patent [19]

Hammond et al.

[11] Patent Number: 5,792,453
[45] Date of Patent: Aug. 11, 1998

[54] GENE TRANSFER-MEDIATED ANGIOGENESIS THERAPY

[75] Inventors: H. Kirk Hammond, La Jolla; Frank J. Giordano, Del Mar; Wolfgang H. Dillmann, Solana Beach, all of Calif.

[73] Assignee: The Regents of the University of California, Oakland, Calif.

[21] Appl. No.: 485,472

[22] Filed: Jun. 7, 1995

(Under 37 CFR 1.47)

Related U.S. Application Data

[63] Continuation-in-part of Ser. No. 396,207, Feb. 28, 1995, abandoned.
[51] Int. Cl.$^6$ ................................................. A01N 63/00
[52] U.S. Cl. ............................ 424/93.21; 435/172.3; 435/320.1; 435/366; 536/23.5
[58] Field of Search .............................. 435/320.1, 369, 435/93.1, 172.3, 366; 514/44; 424/93.21; 536/23.5

[56] References Cited

U.S. PATENT DOCUMENTS 5,443,836  8/1995  Downey et al. ........................ 424/423

FOREIGN PATENT DOCUMENTS

27902/92  6/1993  Australia .
WO 94/11506  5/1994  WIPO .

OTHER PUBLICATIONS

Barr et al., Supplement II Circulation, vol. 84, No. 4, Oct. 1991.
French, Herz 18(4):222–229 (1993).
Giordano and Hammond, Clin Res 42:123A, 1994.
JAMA, Dec. 16, 1992–vol. 268, No. 23, 3285–3286.
Mazur et al., Texas Heart Institute Journal article 21:104–11 (1994).
Barr, E., et al., "Efficient catheter-mediated gene transfer into the heart using replication-defective adenovirus", Gene Therapy, 1:51–58 (1994).
Barr, E., et al., "Somatic Gene Therapy for Cardiovascular Disease", TCM, 4(2):57–63 (1994).
Franz, W-M., et al., "Heart-Specific Targeting of Firefly Luciferase by the Myosin Light Chain–2 Promoter and Developmental Regulation in Transgenic Mice", Circulation Research, 73(4):629–638 (1993).
Franz, W-M., et al., "Characterization of a Cardiac-Selective and Developmentally Upregulated Promotor in Transgenic Mice", Cardioscience, 5(4):235–243 (1994).
French, B. A., et al., "Direct In Vivo Gene Transfer Into Porcine Myocardium Using Replication–Deficient Adenoviral Vectors", Circulation, 90(5):2414–2424 (1994).
French, B. A., et al., "Feasibility and Limitations of Direct In Vivo Gene Transfer Into Porcine Myocardium Using Replication-Deficient Adenoviral Vectors", Circulation, 90:1517 Abstract No. 2785 (1994).

Giordano, F. J., et al., "Reduced Myocardial Ischemia After Recombinant Adenovirus Mediated In–Vivo Fibroblast Growth Factor–5 Gene Transfer", J. Investgative Med., Supplement 2, 43:287A (1995).
Guzman, R. J., et al., "Efficient Gene Transfer Into Myocardium by Direct Injectioin of Adenovirus Vectors", Circulation Research, 73(6):1202–1207 (1993).
Kass-Eisler, A., et al., "Quantitative determination of adenovirus-mediated gene delivery to rat cardiac myocytes in vitro and in vivo", PNAS (USA), 90:11498–11502 (1993).
Klagsbrun, M., et al., "The Fibroblast Growth Factor Family: Structural and Biological Properties", Progress In Growth Factor Research, 1:207–235 (1989).
Marber, M. S., et al., "Overexpression of the Rat Inducible 70–kD Heat Stress Protein in a Transgenic Mouse Increases the Resistance of the Heart to Ischemic Injury", J. Clin. Invest., 95:1446–1456 (1995).
McDonald, P., et al., "Models of Gene Therapy for Myocardial Ischemia", J. Cell. Biochem. Supp., 21A:381, Abstract No. C6–225 (1995).
Mühlhauser, J., et al., "In Vivo Angiogenesis Induced by Recombinant Adenovirus Vectors Coding Either for Secreted or Nonsecreted Forms of Acidic Fibroblast Growth Factor", Human Gene Theraphy, 6:1457–1465 (1995).
Mühlhauser, J., et al., "VEGF$_{165}$ Expressed by a Replication-Deficient Recombinant Adenovirus Vector Induces Angiogenesis In Vivo", Circulation Research, 77(6):1077–1086 (1995).
Plumier, J.-C. L., et al., "Transgenic Mice Expressing the Human Heat Shock Protein 70 Have Improved Post-Ischemic Myocardial Recovery", J. Clin. Invest., 95:1854–1860 (1995).
Williams, R. S., "Southwestern Internal Medicine Conference: Prospects for Gene Therapy of Ischemic Heart Disease", Am. J. Med. Sci., 306(2):129–136 (1993).
Flugelman, Moshe Y., "Inhibition of Intravascular Thrombosis and Vascular Smooth Muscle Cell Proliferation by Gene Therapy", Throm. Haemostasis, 74(1):406–410 (1995).
French, Brent A., et al., "Percutaneous Transluminal In Vivo Gene Transfer by Recombinant Adenovirus in Normal Porcine Coronary Arteries, Atherosclerotic Arteries, and Two Models of Coronary Restenosis", Circulation, 90(5):2402–2013 (1994).

(List continued on next page.)

Primary Examiner—Nancy Degen
Assistant Examiner—Irem Yucel
Attorney, Agent, or Firm—Morrison & Foerster LLP

[57] ABSTRACT

The transgene-inserted replication-deficit adenovirus vector is effectively used in in vivo gene therapy for peripheral vascular disease and heart disease, including myocardial ischemia, by a single intra-femoral artery or intracoronary injection directly conducted deeply in the lumen of the one or both femoral or coronary arteries (or graft vessels) in an amount sufficient for transfecting cells in a desired region.

41 Claims, 5 Drawing Sheets

OTHER PUBLICATIONS

Rowland, Robert T., et al., Potential Gene Therapy Strategies in the Treatment of Cardiovascular Disease, *Am Thorac. Surg.*, 60(3):721–718 (1995).

Pili, et al., 1994, J. of Cellular Biochemistry, Supplement 18A, Jan., 1994, Abstract EZ310.

McGrory, W., et al., 1988, Virology, vol. 163, pp. 614–617.

Gomez–Foix, A., et al., 1992, J. Biological Chemistry, vol. 267, No. 35, pp. 25129–25134.

Orkin, et al., 1995, Report and Recommendations of the Panel to Assess the NIH Investment in Research on Gene Therapy.

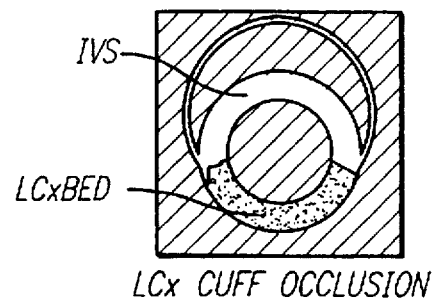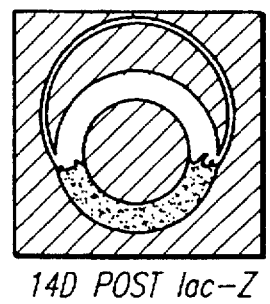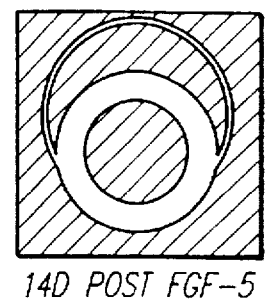
FIG. 4a  FIG. 4b  FIG. 4c
FIG. 4

GENE TRANSFER-MEDIATED ANGIOGENESIS THERAPY

CROSS REFERENCE TO RELATED APPLICATION

This application is a continuation-in-part of U.S. application Ser. No. 08/396,207, filed on Feb. 28, 1995.

STATEMENT REGARDING FORMALLY SPONSORED RESEARCH

This invention was made with Government support under Grant Nos. HL0281201 and HL1768218, awarded by the National Institutes of Health. The Government may have certain rights in this invention.

BACKGROUND

1. Field of the Invention

The present invention relates to gene therapy, more specifically, to virus-mediated and other forms of gene therapy, and to certain adenovirus constructs useful in the delivery of desired genes. More particularly, the invention relates to adenovirus-mediated delivery of genes useful in the promotion of angiogenesis in the heart, and to methods for the treatment of peripheral vascular disease and diseases of the heart such as myocardial ischemia using such vectors.

2. Background of the Art

It has been reported by the American Heart Association (1995 Statistical Supplement), that there are about 60 million adults in the United States that have cardiovascular disease, including 11 million adults who have coronary heart disease. Cardiovascular diseases are responsible for almost a million deaths annually in the United States, representing over 40% of all deaths. In 1995, 1.5 million adults in the United States will carry the diagnosis of angina pectoris, experiencing transient periods of myocardial ischemia resulting in chest pain. About 350,000 new cases of angina occur each year in the United States.

Myocardial ischemia occurs when the heart muscle does not receive an adequate blood supply and is thus deprived of necessary levels of oxygen and nutrients. The most common cause of myocardial ischemia is atherosclerosis, which causes blockages in the blood vessels (coronary arteries) that provide blood flow to the heart muscle. Present treatments include pharmacological therapies, coronary artery bypass surgery and percutaneous revascularization using techniques such as balloon angioplasty. Standard pharmacological therapy is predicated on strategies that involve either increasing blood supply to the heart muscle or decreasing the demand of the heart muscle for oxygen and nutrients. Increased blood supply to the myocardium is achieved by agents such as calcium channel blockers or nitroglycerin. These agents are thought to increase the diameter of diseased arteries by causing relaxation of the smooth muscle in the arterial walls. Decreased demand of the heart muscle for oxygen and nutrients is accomplished either by agents that decrease the hemodynamic load on the heart, such as arterial vasodilators, or those that decrease the contractile response of the heart to a given hemodynamic load, such as beta-adrenergic receptor antagonists. Surgical treatment of ischemic heart disease is based on the bypass of diseased arterial segments with strategically placed bypass grafts (usually saphenous vein or internal mammary artery grafts). Percutaneous revascularization is based on the use of catheters to reduce the narrowing in diseased coronary arteries. All of these strategies are used to decrease the number of, or to eradicate, ischemic episodes, but all have various limitations.

Preliminary reports describe new vessel development in the heart through the direct injection of angiogenic proteins or peptides to treat myocardial ischemia. The several members of the fibroblast growth factor (FGF) family (namely acidic fibroblast growth factor, aFGF; basic fibroblast growth factor, bFGF; fibroblast growth factor-5, FGF-5 and others) have been implicated in the regulation of angiogenesis during growth and development. The role of aFGF protein in promoting angiogenesis in adult animals, for example, was the subject of a recent report. It states that aFGF protein, within a collagen-coated matrix, placed in the peritoneal cavity of adult rats, resulted in a well vascularized and normally perfused structure (Thompson, et al., PNAS 86:7928–7932, 1989). Injection of bFGF protein into adult canine coronary arteries during coronary occlusion reportedly led to decreased myocardial dysfunction, smaller myocardial infarctions, and increased vascularity in the bed at risk (Yanagisawa-Miwa, et al., Science 257:1401–1403, 1992). Similar results have been reported in animal models of myocardial ischemia using bFGF protein (Harada, et al., J Clin Invest 94:623–630, 1994, Unger, et al., Am J Physiol 266:H1588–H1595, 1994).

A prerequisite for achieving an angiogenic effect with these proteins however, has been the need for repeated or long term delivery of the protein, which limits the utility of using these proteins to stimulate angiogenesis in clinical settings. In other words, successful therapy in humans would require sustained and long-term infusion of one or more of these angiogenic peptides or proteins, which are themselves prohibitively expensive and which would need to be delivered by catheters placed in the coronary arteries, further increasing the expense and difficulty of treatment.

Recently, various publications have postulated on the uses of gene transfer for the treatment or prevention of disease, including heart disease. See, for example, Mazur et al., "Coronary Restenosis and Gene Therapy," *Molecular and Cellular Pharmacology*, 21:104–111, 1994; French, "Gene Transfer and Cardiovascular Disorders," *Herz* 18:222–229, 1993; Williams, "Prospects for Gene Therapy of Ischemic Heart Disease," *American Journal of Medical Sciences* 306:129–136, 1993; Schneider and French, "The Advent of Adenovirus: Gene Therapy for Cardiovascular Disease," *Circulation* 88:1937–1942, 1993. Another publication, Leiden et al, International Patent Application Number PCT/US93/11133, entitled "Adenovirus-Mediated Gene Transfer to Cardiac and Vascular Smooth Muscle," reports on the use of adenovirus-mediated gene transfer for the purpose of regulating function in cardiac vascular smooth muscle cells. Leiden et al. states that a recombinant adenovirus comprising a DNA sequence that encodes a gene product can be delivered to a cardiac or vascular smooth muscle cell and the cell maintained until that gene product is expressed. According to Leiden et al., muscle cell function is regulated by altering the transcription of genes and changes in the production of a gene transcription product, such as a polynucleotide or polypeptide. That polynucleotide or polypeptide, report Leiden et al., interacts with the cardiac or smooth muscle cell to regulate function of that cell. Leiden et al. states that this regulation can be accomplished whether the cell is situated in vitro, in situ, or in vivo. Leiden et al. describes a gene transfer method comprising obtaining an adenoviral construct containing a gene product by co-transfecting a gene product-inserted replication deficient adenovirus type 5 (with the CMV promoter) into 293 cells together with a plasmid carrying a complete adenovirus genome such as plasmid JM17; propagating the resulting adenoviral construct in 293 cells; and delivering the adenoviral construct to cardiac muscle or vascular smooth muscle cells by directly injecting the vector into the cells.

There are impediments to successful gene transfer to the heart using adenovirus vectors. For example, the insertion of a transgene into a rapidly dividing cell population will result in substantially reduced duration of transgene expression. Examples of such cells include endothelial cells, which make up the inner layer of all blood vessels, and fibroblasts which are dispersed throughout the heart. Targeting the transgene so that only the desired cells will receive and express the transgene, and the transgene will not be systemically distributed, are also critically important considerations. If this is not accomplished, systemic expression of the transgene and problems attendant thereto will result. For example, inflammatory infiltrates have been documented after adenovirus-mediated gene transfer in liver (Yang, et al. *Proc. Natl. Acad. Sci.* (U.S.A.) 91:4407, 1994). Finally, with regard to adenovirus-mediated gene transfer of FGF-5 for the in vivo stimulation of angiogenesis, we have discovered that the injected viral material can induce serious, often life-threatening cardiac arrhythmias.

The invention described and claimed herein addresses and overcomes these and other problems associated with the prior art.

BRIEF DESCRIPTION OF THE FIGURES

FIG. 4A-4C show diagrams corresponding to myocardial contrast echocardiographs (not shown). White areas denote contrast enhancement (more blood flow) and dark areas denote decreased blood flow. FIG. 4A shows acute LCx occlusion in a normal pig, FIG. 4B shows 14±1 days after lacZ gene transfer, and FIG. 4C shows 14±1 days after gene transfer with FGF-5.

SUMMARY OF THE INVENTION

Figure 1:
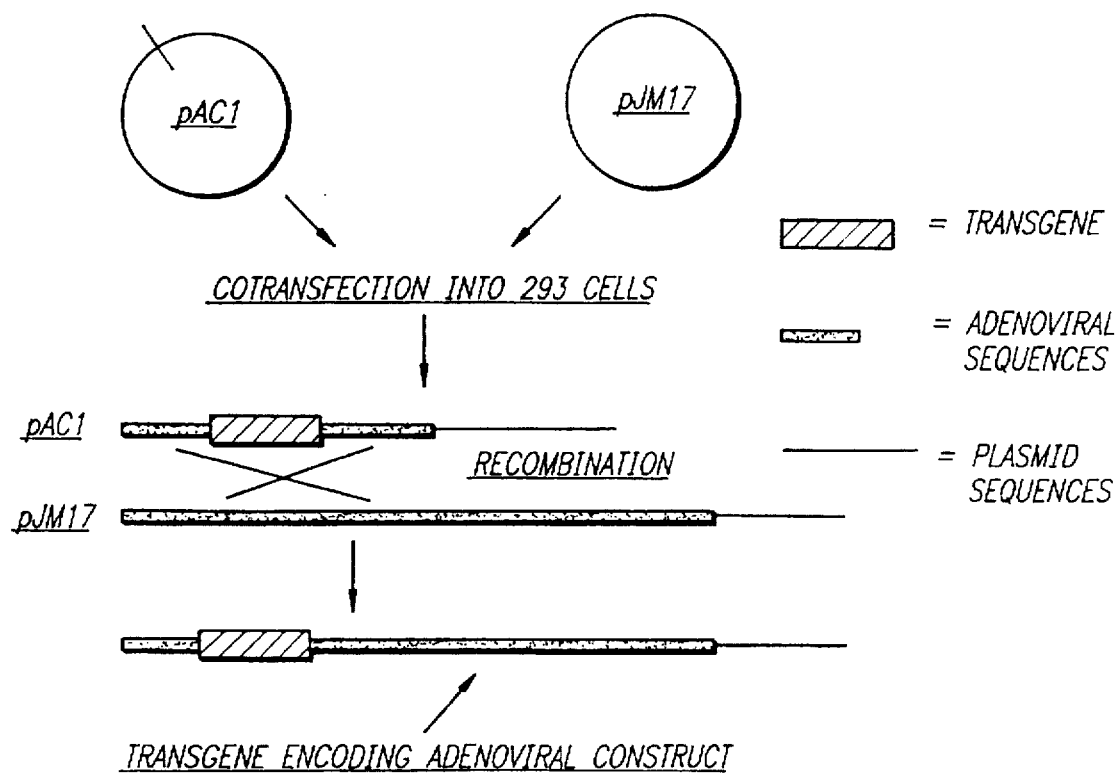
FIG. 1 is a schematic figure which shows rescue recombination construction of a transgene encoding adenovirus.

The present invention is directed to a gene therapy approach useful in the treatment of heart disease, preferably myocardial ischemia, and peripheral vascular disease. One objective of the present invention is to provide a method for treating heart disease in which an angiogenic protein or peptide, preferably FGF-5, is produced to a therapeutically significant degree in the myocardium continuously for sustained periods by targeting the heart with a vector construct containing a gene for said angiogenic protein or peptide, preferably a replication-deficient adenovirus construct, delivered through intracoronary injection, preferably by catheter introduced substantially (typically at least about 1 cm) beyond the ostium of one or both coronary arteries or one or more saphenous vein or internal mammary artery grafts.

Another aspect of the present invention is a method for treating a heart disease in a patient having myocardial ischemia, comprising delivering a transgene-inserted replication-deficient adenoviral vector to the myocardium of the patient by intracoronary injection, preferably a single injection of the vector, directly into one or both coronary arteries (or grafts), to transfect cardiac myocytes in the affected myocardium, said vector comprising a transgene coding for an angiogenic protein or peptide such as FGF-5, aFGF, bFGF or VEGF (vascular endothelial growth factor), and expressing the transgene in the heart, thereby promoting angiogenesis in the affected region of the myocardium. By injecting the vector stock containing no wild-type virus deeply into the lumen of one or both coronary arteries (or grafts), preferably into both the right and left coronary arteries (or grafts), and preferably in an amount of $10^7$–$10^{13}$ viral particles as determined by optical densitometry (more preferably $10^9$–$10^{11}$ viral particles), it is possible to locally transfect a desired number of cells, especially cardiac myocytes, in the affected myocardium with angiogenic protein- or peptide-encoding genes, thereby maximizing therapeutic efficacy of gene transfer, and minimizing undesirable angiogenesis at extracardiac sites and the possibility of an inflammatory response to viral proteins. If a ventricular myocyte-specific promoter is used, for example, the promoter more securely enables expression limited to the cardiac myocytes so as to avoid the potentially harmful effects of angiogenesis in non-cardiac tissues such as the retina.

In another aspect, the present invention provides a filtered, injectable adenoviral vector preparation, comprising a recombinant adenoviral vector, preferably in a final viral titer of $10^7$–$10^{13}$ viral particles, said vector containing no wild-type virus and comprising a partial adenoviral sequence from which one or more required adenovirus genes conferring replication competence, for example, the E1A/E1B genes have been deleted, and a transgene coding for an angiogenic protein or peptide such as angiogenic aFGF, bFGF and VEGF, driven by a promoter flanked by the partial adenoviral sequence; and a pharmaceutically acceptable carrier. By using this injectable adenoviral vector preparation, it is possible to perform effective adenovirus-mediated FGF-5 gene transfer for the treatment of clinical myocardial ischemia or peripheral vascular disease without any undesirable effects.

In a further aspect, the present invention provides a method of production of a viral stock containing a recombinant vector capable of expressing an angiogenic protein or peptide in vivo in the myocardium, comprising the steps of cloning a transgene, preferably coding for an angiogenic protein or peptide such as FGF-5, aFGF, bFGF and VEGF, into a plasmid containing a promoter and a polylinker flanked by partial adenoviral sequences of the left end of the human adenovirus 5 genome from which one or more required adenovirus genes conferring replication competence, for example, the E1A/E1B genes have been deleted; co-transfecting said plasmid into mammalian cells transformed with the missing replication-requiring genes, with a plasmid which contains the entire human adenoviral 5 genome and an additional insert making the plasmid too large to be encapsidated, whereby rescue recombination takes place between the transgene-inserted plasmid and the plasmid having the entire adenoviral genome so as to create a recombinant genome containing the transgene without the replication-requiring genes, said recombinant genome being sufficiently small to be encapsidated; identifying successful recombinants in cell cultures; propagating the resulting recombinant in mammalian cells transformed with the absent replication-requiring genes; and purifying the propagated recombinants so as to contain the recombinant vector, without wild-type virus therein, and passing the purified vector through a filter, preferably 10–50 micron filter, more preferably a 30 micron filter.

In yet another aspect, a recombinant adenovirus expressing an angiogenic peptide or protein will be delivered by catheter into the proximal portion of the femoral artery or arteries, thereby effecting gene transfer into the cells of the skeletal muscles receiving blood flow from the femoral arteries. This will provide an angiogenic stimulus that will result in angiogenesis in skeletal muscle of the legs and will serve as a treatment for peripheral vascular disease, a disease that is characterized by insufficient blood supply to muscles of the legs.

DETAILED DESCRIPTION OF THE PREFERRED EMBODIMENTS

Transgenes Encoding Angiogenic Proteins and Peptides

In the present invention, various protein or peptide growth factors that are capable of improving myocardial blood flow to ischemic regions of the heart (or skeletal muscle in the case of peripheral vascular disease) can be used. As an angiogenic protein or peptide to be expressed, an angiogenic protein or peptide such as aFGF, bFGF, and FGF-5 can be exemplified. The angiogenic activity of the FGF family is reasonably well established in the setting of protein infusions (Yanagisawa-Miwa, et al., *Science* 257:1401–1403, 1992, Harada, et al., *J Clin Invest* 94:623–630, 1994, Unger, et al., *Am J Physiol* 266:H1588–H1595, 1994). The gene for VEGF (vascular endothelial growth factor), a potent stimulater of new vessel growth, can also be used. Success of the gene transfer approach requires both synthesis of the gene product and secretion from the transfected cell. From this point of view, a gene encoding FGF-5 is preferred and is preferably selected to include a sequence encoding a signal peptide, thus directing that the gene product, once expressed, will gain access to the cardiac (or skeletal muscle) interstitium and induce angiogenesis.

Helper Independent Replication Deficient Human Adenovirus 5 System

In general, the gene of interest is transferred to the heart (or skeletal muscle), including cardiac myocytes (and skeletal myocytes), in vivo and directs constitutive production of the encoded protein. Several different gene transfer approaches are feasible. Preferred is the helper-independent replication deficient human adenovirus 5 system. Using this system, we have demonstrated transfection greater than 60% of myocardial cells in vivo by a single intracoronary injection (Giordano and Hammond, *Clin. Res.* 42: 123A, 1994). Non-replicative recombinant adenoviral vectors are particularly useful in transfecting coronary endothelium and cardiac myocytes resulting in highly efficient transfection after intracoronary injection. The same will be true for transfecting desired cells of the peripheral vascular system.

The recombinant adenoviral vectors based on the human adenovirus 5 (*Virology* 163:614–617, 1988) are missing essential early genes from the adenoviral genome (usually E1A/E1B), and are therefore unable to replicate unless grown in permissive cell lines that provide the missing gene products in trans. In place of the missing adenoviral genomic sequences, a transgene of interest can be cloned and expressed in tissue/cells infected with the replication deficient adenovirus. Although adenovirus-based gene transfer does not result in integration of the transgene into the host genome (less than 0.1% adenovirus-mediated transfections result in transgene incorporation into host DNA), and therefore is not stable, adenoviral vectors can be propagated in high titer and transfect non-replicating cells. Although the transgene is not passed to daughter cells, this is acceptable for gene transfer to adult skeletal muscle and cardiac myocytes, which do not divide. Retroviral vectors provide stable gene transfer, and high titers are now obtainable via retrovirus pseudotyping (Burns, et al., *Proc Natl Acad Sci (USA)* 90:8033–8037, 1993), but current retroviral vectors are unable to transduce nonreplicating cells (adult skeletal muscle and cardiac myocytes) efficiently. In addition, the potential hazards of transgene incorporation into host DNA are not warranted if short-term gene transfer is sufficient. Indeed, we have discovered that a limited duration expression of an angiogenic protein is sufficient for substantial angiogenesis, and transient gene transfer for cardiovascular disease and peripheral disease processes is therapeutically adequate.

Human 293 cells, which are human embryonic kidney cells transformed with adenovirus E1A/E1B genes, typify useful permissive cell lines. However, other cell lines which allow replication-deficient adenoviral vectors to propagate therein can be used, including HeLa cells.

Construction of Recombinant Adenoviral Vectors

All adenoviral vectors used in the present invention can be constructed by the rescue recombination technique described in Graham, Virology 163:614–617, 1988. Briefly, the transgene of interest is cloned into a shuttle vector that contains a promoter, polylinker and partial flanking adenoviral sequences from which E1A/E1B genes have been deleted. As the shuttle vector, plasmid pAC1 (*Virology* 163:614–617, 1988) (or an analog) which encodes portions of the left end of the human adenovirus 5 genome (*Virology* 163:614–617, 1988) minus the early protein encoding E1A and E1B sequences that are essential for viral replication, and plasmid ACCMVPLPA (*J Biol Chem* 267:25129–25134, 1992) which contains polylinker, the CMV promoter and SV40 polyadenylation signal flanked by partial adenoviral sequences from which the EA/E1B genes have been deleted can be exemplified. The use of plasmid PAC1 or ACCMVPLA facilitates the cloning process. The shuttle vector is then co-transfected with a plasmid which contains the entire human adenoviral 5 genome with a length too large to be encapsidated, into 293 cells. Co-transfection can be conducted by calcium phosphate precipitation or lipofection (*Biotechniques* 15:868–872, 1993). Plasmid JM17 encodes the entire human adenovirus 5 genome plus portions of the vector pBR322 including the gene for ampicillin resistance (4.3 kb). Although JM17 encodes all of the adenoviral proteins necessary to make mature viral particles, it is too large to be encapsidated (40 kb versus 36 kb for wild type). In a small subset of co-transfected cells, rescue recombination between the transgene containing the shuttle vector such as plasmid pAC1 and the plasmid having the entire adenoviral 5 genome such as plasmid pJM17 provides a recombinant genome that is deficient in the E1A/E1B sequences, and that contains the transgene of interest but secondarily loses the additional sequence such as the pBR322 sequences during recombination, thereby being small enough to be encapsidated (see FIG. 1). With respect to the above method, we have reported successful results (Giordano, et al. *Circulation* 88:1–139, 1993, and Giordano and Hammond, *Clin Res* 42:123A, 1994). The CMV driven β-galactosidase encoding adenovirus HCMVSP1lacZ (*CLIN RES* 42:123A, 1994) can be used to evaluate efficiency of gene transfer using X-gal treatment.

The initial mode of gene transfer uses adenoviral vectors as delineated above. The advantages of these vectors include the ability to effect high efficiency gene transfer (more than 60% of target organ cells transfected in vivo), the ease of obtaining high titer viral stocks and the ability of these vectors to effect gene transfer into cells such as cardiac myocytes which do not divide.

Tissue-Specific Promoters

The present invention also contemplates the use of cell targeting not only by delivery of the transgene into the coronary artery, or femoral artery, for example, but also the use of tissue-specific promoters. By fusing, for example, tissue-specific transcriptional control sequences of left ventricular myosin light chain-2 ($MLC_{2V}$) or myosin heavy chain (MHC) to a transgene such as the FGF-5 gene within the adenoviral construct, transgene expression is limited to ventricular cardiac myocytes. The efficacy of gene expression and degree of specificity provided by $MLC_{2V}$ and MHC promoters with lacZ have been determined, using the recombinant adenoviral system of the present invention. Cardiac-specific expression has been reported previously by Lee, et al. (*J Biol Chem* 267:15875–15885,1992). The $MLC_{2V}$ promoter is comprised of 250 bp, and fits easily within the adenoviral-5 packaging constraints. The myosin heavy chain promoter, known to be a vigorous promoter of transcription, provides a reasonable alternative cardiac-specific promoter and is comprised of less than 300 bp. Other promoters, such as the troponin-C promoter, while highly efficacious and sufficiently small, lacks adequate tissue specificity. By using the $MLC_{2V}$ or MHC promoters and delivering the transgene in vivo, it is believed that the cardiac myocyte alone (that is without concomitant expression in endothelial cells, smooth muscle cells, and fibroblasts within the heart) will provide adequate expression of an angiogenic protein such as FGF-5 to promote angiogenesis. Limiting expression to the cardiac myocyte also has advantages regarding the utility of gene transfer for the treatment of clinical myocardial ischemia. By limiting expression to the heart, one avoids the potentially harmful effect of angiogenesis in non-cardiac tissues such as the retina. In addition, of the cells in the heart, the myocyte would likely provide the longest transgene expression since the cells do not undergo rapid turnover; expression would not therefore be decreased by cell division and death as would occur with endothelial cells. Endothelial-specific promoters are already available for this purpose (Lee, et al., *J Biol Chem* 265:10446–10450, 1990).

In the present invention, with regard to the treatment of heart disease, targeting the heart by intracoronary injection with a high titer of the vector and transfecting all cell types is presently preferred.

Propagation and Purification of Adenovirus Vectors

Successful recombinant vectors can be plaque purified according to standard methods. The resulting viral vectors are propagated on 293 cells which provide E1A and E1B functions in trans to titers in the preferred $10^{10}$–$10^{12}$ viral particles/ml range. Cells can be infected at 80% confluence and harvested 48 hours later. After 3 freeze-thaw cycles the cellular debris is pelleted by centrifugation and the virus purified by CsCl gradient ultracentrifugation (double CsCl gradient ultracentrifugation is preferred). Prior to in vivo injection, the viral stocks are desalted by gel filtration through Sepharose columns such as G25 Sephadex. The product is then filtered through a 30 micron filter, thereby reducing deleterious effects of intracoronary injection of unfiltered virus (life threatening cardiac arrhythmias) and promoting efficient gene transfer. The resulting viral stock has a final viral titer in the range of $10^{10}$–$10^{12}$ viral particles/ml. The recombinant adenovirus must be highly purified, with no wild-type (potentially replicative) virus. Impure constructs can cause an intense immune response in the host animal. From this point of view, propagation and purification may be conducted to exclude contaminants and wild-type virus by, for example, identifying successful recombinants with PCR using appropriate primers, conducting two rounds of plaque purification, and double CsCl gradient ultracentrifugation. Additionally, we have found that the problems associated with cardiac arrhythmias induced by adenovirus vector injection into patients can be avoided by filtration of the recombinant adenovirus through an appropriately-sized filter prior to intracoronary injection. This strategy also appears to substantially improve gene transfer and expression.

Delivery of Recombinant Adenovirus Vectors

The viral stock can be in the form of an injectable preparation containing pharmaceutically acceptable carrier such as saline, for example, as necessary. The final titer of the vector in the injectable preparation is preferably in the range of $10^7$–$10^{13}$ viral particles which allows for effective gene transfer. Other pharmaceutical carriers, formulations and dosages are described below. The adenovirus transgene constructs are delivered to the myocardium by direct intracoronary (or graft vessel) injection using standard percutaneous catheter based methods under fluoroscopic guidance, at an amount sufficient for the transgene to be expressed to a degree which allows for highly effective therapy. The injection should be made deeply into the lumen (about 1 cm within the arterial lumen) of the coronary arteries (or graft vessel), and preferably be made in both coronary arteries, as the growth of collateral blood vessels is highly variable within individual patients. By injecting the material directly into the lumen of the coronary artery by coronary catheters, it is possible to target the gene rather effectively, and to minimize loss of the recombinant vectors to the proximal aorta during injection. We have found that gene expression when delivered in this manner does not occur in hepatocytes and viral RNA cannot be found in the urine at any time after intracoronary injection. Any variety of coronary catheter, or a Stack perfusion catheter, for example, can be used in the present invention. In addition, other techniques known to those having ordinary skill in the art can be used for transfer of genes to the arterial wall.

For the treatment of peripheral vascular disease, a disease characterized by insufficient blood supply to the legs, recombinant adenovirus expressing an angiogenic peptide or protein will be delivered by a catheter that will be inserted into the proximal portion of the femoral artery or arteries, thereby effecting gene transfer into the cells of the skeletal muscles receiving blood flow from the femoral arteries. This will provide an angiogenic stimulus that will result in angiogenesis in skeletal muscle of the legs.

Animal Model of Myocardial Ischemia

Important prerequisites for successful studies on gene therapy are (a) constitution of an animal model which is applicable to clinical myocardial ischemia which can provide useful data regarding mechanisms for angiogenesis in the setting of myocardial ischemia, and (b) accurate evaluation of the effects of gene transfer. From this point of view, none of the prior art is satisfactory. We have made use of a porcine model of myocardial ischemia that mimics clinical coronary artery disease. Placement of an ameroid constrictor around the left circumflex (LCx) coronary artery results in gradual complete closure (within 7 days of placement) with minimal infarction (1 % of the left ventricle, 4±1% of the LCx bed) (Roth, et al. *Circulation* 82:1778, 1990, Roth, et al. *Am J Physiol* 235:H1279, 1987, White, et al. *Circ Res* 71:1490, 1992, Hammond, et al. *Cardiol* 23:475, 1994, and Hammond, et al. *J Clin Invest* 92:2644, 1993). Myocardial function and blood flow are normal at rest in the region previously perfused by the occluded artery (referred to as the ischemic region), due to collateral vessel development, but blood flow reserve is insufficient to prevent ischemia when myocardial oxygen demands increase. Thus, the LCx bed is subject to episodic ischemia, analogous to clinical angina pectoris. Collateral vessel development and flow-function relationships are stable within 21 days of ameroid placement, and remain unchanged for four months (Roth, et al. *Circulation* 82:1778, 1990, Roth, et al. *Am J Physiol* 235:H1279, 1987, White, et al. *Circ Res* 71:1490, 1992). It has been documented by telemetry that animals have period ischemic dysfunction in the bed at risk throughout the day, related to abrupt increases in heart rate during feeding, interruptions by personnel, etc. (unpublished data). Thus, the model has a bed with stable but inadequate collateral vessels, and is subject to periodic ischemia. Another distinct advantage of the model is that there is a normally perfused and functioning region (the LAD bed) adjacent to an abnormally perfused and functioning region (the LCx bed), thereby offering a control bed within each animal.

Myocardial contrast echocardiography was used to estimate regional myocardial perfusion. The contrast material is composed of microaggregates of galactose and increases the echogenicity (whiteness) of the image. The microaggregates distribute into the coronary arteries and myocardial walls in a manner that is proportional to blood flow (Skyba, et al. *Circulation* 90:1513-1521, 1994). It has been shown that peak intensity of contrast is closely correlated with myocardial blood flow as measured by microspheres (Skyba, et al. *Circulation* 90:1513-1521, 1994). To document that the echocardiographic images employed in the present invention were accurately identifying the LCx bed, and that myocardial contrast echocardiography could be used to evaluate myocardial blood flow, a hydraulic cuff occluder was placed around the proximal LCx adjacent to the ameroid.

In the present study, when animals were sacrificed, the hearts were perfusion-fixed (glutaraldehyde, physiological pressures, in situ) in order to quantitate capillary growth by microscopy. PCR was used to detect angiogenic protein DNA and mRNA in myocardium from animals that had received gene transfer. In addition, as described below, two weeks after gene transfer, myocardial samples from all five lacZ-infected animals show substantial β-galactosidase activity on histological inspection. Finally, using a polyclonal antibody to an angiogenic protein, angiogenic protein expression in cells and myocardium from animals that had received gene transfer was demonstrated.

The strategy for therapeutic studies included the timing of transgene delivery, the route of administration of the transgene, and choice of the angiogenic gene. In the ameroid model of myocardial ischemia, gene transfer was performed after stable but insufficient collateral vessels had developed. Previous studies using the ameroid model involved delivery of angiogenic peptides during the closure of the ameroid, prior to the development of ischemia and collateral vessels. However, this strategy was not employed for several reasons. First, previous studies are not suitable for closely duplicating the conditions that would be present in the treatment of clinical myocardial ischemia in which gene transfer would be given in the setting of ongoing myocardial ischemia; previous studies are analogous to providing the peptide in anticipation of ischemia, and are therefore less relevant. Second, it was presumed, based upon previous studies in cell culture, that an ischemic stimulus in conjunction with the peptide would be the optimal milieu for the stimulation of angiogenesis. This could optimally be achieved by delivery of the transgene at a time when myocardial ischemia was already present. Linked to these decisions was the selection of the method to achieve transgene delivery. The constraint that the technique should be applicable for the subsequent treatment of patients with coronary disease, made several approaches untenable (continuous infusion of a peptide into the coronary artery, direct plasmid injection into the heart, coating the heart with a resin containing the peptide to provide long-term slow release). Finally, the pig model provided an excellent means to follow regional blood flow and function before and after gene delivery. The use of control animals that received the same recombinant adenovirus construct but with a reporter gene provided a control for these studies. Those skilled in the art will understand that the results described below in pigs are predictive of results in humans. The pig has a native coronary circulation very similar of that of humans, including the absence of native coronary collateral vessels.

Therapeutic Applications

The replication deficient recombinant adenovirus vectors of the present invention allow for highly efficient gene transfer in vivo without cytopathic effect or inflammation in the areas of gene expression. Based on these results, described further in the below Examples, it is seen that a high enough degree of in vivo gene transfer to effect in vivo functional changes is achieved.

In the case of treating a heart disease, the gene transfer of an angiogenic protein by intracoronary injection will promote angiogenesis. Thus, treatment of ischemia can be conducted after observation of initial ischemic episodes. In addition, after gene transfer, capillary number, blood flow and function will increase in the ischemic region. Application of these techniques clinically will be of great utility, especially initially in those with inoperative coronary artery disease and disabling angina pectoris. The data of the present invention demonstrate that gene transfer of a recombinant adenovirus expressing fibroblast growth factor-5 (FGF-5) is effective in substantially reducing myocardial ischemia.

Compositions or products of the invention may conveniently be provided in the form of formulations suitable for intracoronary administration. A suitable administration format may best be determined by a medical practitioner for each patient individually. Suitable pharmaceutically acceptable carriers and their formulation are described in standard formulations treatises, e.g., *Remington's Pharmaceuticals Sciences* by E. W. Martin. See also Wang, Y. J. and Hanson, M. A. "Parental Formulations of Proteins and Peptides: Stability and Stabilizers," *Journals of Parental Sciences and Technology*, Technical Report No. 10, Supp. 42:2S (1988). Vectors of the present invention should preferably be formulated in solution at neutral pH, for example, about pH 6.5 to about pH 8.5, more preferably from about pH 7 to 8, with an excipient to bring the solution to about isotonicity, for example, 4.5% mannitol or 0.9% sodium chloride, pH buffered with art-known buffer solutions, such as sodium phosphate, that are generally regarded as safe, together with an accepted preservative such as metacresol 0.1% to 0.75%, more preferably from 0.15% to 0.4% metacresol. The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. Sodium chloride is preferred particularly for buffers containing sodium ions. If desired, solutions of the above compositions may also be prepared to enhance shelf life and stability. The therapeutically useful compositions of the invention are prepared by mixing the ingredients following generally accepted procedures. For example, the selected components may be mixed to produce a concentrated mixture which may then be adjusted to the final concentration and viscosity by the addition of water and/or a buffer to control pH or an additional solute to control tonicity.

For use by the physician, the compositions will be provided in dosage form containing an amount of a vector of the invention which will be effective in one or multiple doses to induce angiogenesis at a selected level. As will be recognized by those in the field, an effective amount of therapeutic agent will vary with many factors including the age and weight of the patient, the patient's physical condition, and the level of angiogenesis to be obtained, and other factors.

The effective does of the compounds of this invention will typically be in the range of at least about $10^7$ viral particles, preferably about $10^9$ viral particles, and more preferably about $10^{11}$ viral particles. The number of viral particles may, but preferably does not exceed 1013. As noted, the exact dose to be administered is determined by the attending clinician, but is preferably in 1 ml phosphate buffered saline.

The presently preferred mode of administration in the case of heart disease is by intracoronary injection to one or both coronary arteries (or to one or more saphenous vein or internal mammary artery grafts) using an appropriate coronary catheter. The presently preferred mode of administration in the case of peripheral vascular disease is by injection into the proximal portion of the femoral artery or arteries using an appropriate arterial catheter.

To assist in understanding the present invention, the following Examples are provided which describe the results of a series of experiments. The experiments relating to this invention should not, of course, be construed as specifically limiting the invention and such variations of the invention, now know or later developed, which would be within the purview of one skilled in the art are considered to fall within the scope of the invention as described herein and hereinafter claimed.

EXAMPLE 1

Adenoviral Constructs

A helper independent replication deficient human adenovirus 5 system was used. The genes of interest were lacZ and FGF-5. The full length cDNA for human FGF-5 was released from plasmid pLTR122E (Zhen, et al. *Mol Cell Biolo* 8:3487, 1988) as a 1.1 kb ECOR1 fragment which includes 981 bp of the open reading frame of the gene, and cloned into the polylinker of plasmid ACCMVPLPA which contains the CMV promoter and SV40 polyadenylation signal flanked by partial adenoviral sequences from which the E1A and E1B genes (essential for viral replication) had been deleted. This plasmid was co-transfected (lipofection) into 293 cells with plasmid JM17 which contained the entire human adenoviral 5 genome with an additional 4.3 kb insert making pJM17 too large to be encapsidated. Homologous rescue recombination resulted in adenoviral vectors containing the transgene in the absence of E1A/E1B sequences. Although these recombinants were nonreplicative in mammalian cells, they could propagate in 293 cells which had been transformed with E1A/E1B and provided these essential gene products in trans. Transfected cells were monitored for evidence of cytopathic effect which usually occurred 10–14 days after transfection. To identify successful recombinants, cell supernatant from plates showing a cytopathic effect was treated with proteinase K (50 mg/ml with 0.5% sodium dodecyl sulfate and 20 mM EDTA) at 56° C. for 60 minutes, phenol/chloroform extracted and ethanol precipitated. Successful recombinants were then identified with PCR using primers (*Biotechniques* 15:868–872, 1993) complementary to the CMV promoter and SV40 polyadenylation sequences to amplify the insert (the expected 1.1 kb fragment), and primers (*Biotechniques* 15:868–872, 1993) designed to concomitantly amplify adenoviral sequences. Successful recombinants then underwent two rounds of plaque purification. Viral stocks were propagated in 293 cells to titers ranging between $10^{10}$ and $10^{12}$ viral particles, and were purified by double CsCl gradient centrifugation prior to use. Recombinant adenoviruses encoding β-galactosidase, or FGF-5 were constructed using full length cDNAs. The system used to generate recombinant adenoviruses imposed a packing limit of 5 kb for transgene inserts. The genes proposed, driven by the CMV promoter and with the SV40 polyadenylation sequences were less than 4 kb, well within the packaging constraints. Recombinant vectors were plaque purified by standard procedures. The resulting viral vectors were propagated on 293 cells to titers in the $10^{10}$–$10^{12}$ viral particles range. Cells were infected at 80% confluence and harvested at 36–48 hours. After freeze-thaw cycles the cellular debris was pelleted by standard centrifugation and the virus further purified by double CsCl gradient ultracentrifugation (discontinuous 1.33/1.45 CsCl gradient; cesium prepared in 5 mM Tris, 1 mM EDTA (pH 7.8); 90,000×g (2 hr), 105,000×g (18 hr)). Prior to in vivo injection, the viral stocks were desalted by gel filtration through Sepharose columns such as G25 Sephadex. The resulting viral stock had a final viral titer in the $10^{10}$–$10^{12}$ viral particles range. The adenoviral construct was highly purified, with no wild-type (potentially replicative) virus.

EXAMPLE 2

Adult Rat Cardiomyocytes in Cell Culture

Adult rat cardiomyocytes were prepared by Langendorf perfusion with a collagenase containing perfusate according to standard methods. Rod shaped cells were cultured on laminin coated plates and at 24 hours were infected with the β-galactosidase-encoding adenovirus obtained in the above Example 1 at a multiplicity of infection of 1:1. After a further 36 hour period the cells were fixed with glutaraldehyde and incubated with X-gal. Consistently 70–90% of adult myocytes expressed the β-galactosidase transgene after infection with the recombinant adenovirus. At a multiplicity of infection of 1–2:1 there was no cytotoxicity observed.

EXAMPLE 3

Porcine Myocardium In Vivo

The β-galactosidase-encoding adenoviral vector obtained in Example 1 was propagated in permissive 293 cells and purified by CsCl gradient ultracentrifugation with a final viral titer of $1.5 \times 10^{10}$ viral particles, based on the procedures of Example 1. An anesthetized, ventilated 40 kg pig underwent thoracotomy. A 26 gauge butterfly needle was inserted into the mid left anterior descending (LAD) coronary artery and the vector ($1.5 \times 10^{10}$ viral particles) was injected in a 2 ml volume. The chest was closed and the animal allowed to recover. On the fourth post-injection day the animal was killed. The heart fixed with glutaraldehyde, sectioned and incubated with X-gal for 16.5 hours. After imbedding and sectioning the tissue was counterstained with eosin.

Microscopic analysis of tissue sections (transmural sections of LAD bed 96 hours after intracoronary injection of adenovirus containing lacZ) revealed a significant magnitude of gene transfer observed in the LAD coronary bed with many tissue sections demonstrating greater than 50–60% of the cells staining positively for β-galactosidase. Areas of the myocardium remote from the LAD circulatory bed did not demonstrate X-gal staining and served as a negative control, while diffuse expression of a gene was observed in myocytes and in endothelial cells. The majority of myocytes showed β-galactosidase activity (blue stain), and, in subsequent studies using closed-chest intracoronary injection, similar activity was present 14 days after gene transfer (n=8). There was no evidence of inflammation or necrosis in areas of gene expression

EXAMPLE 4

Porcine Ischemia Model

Animals included 18 domestic pigs (30–40 kg). A left thoracotomy was performed under sterile conditions for instrumentation. (Hammond, et al. *J Clin Invest* 92:2644–2652, and Roth, et al. *J Clin Invest* 91:939–949, 1993). Catheters were placed in the left atrium and aorta, providing a means to measure regional blood flow, and to monitor pressures. Wires were sutured on the left atrium to permit ECG recording and atrial pacing. Finally, an ameroid was placed around the proximal LCx. After a stable degree of ischemia had developed, the treatment group (n=11) received an adenoviral construct that included FGF-5 (an angiogenic gene), driven by a CMV promoter. Control animals (n=7) received gene transfer with an adenoviral construct that included a reporter gene, lacZ, driven by a CMV promoter.

Studies were initiated 35±3 days after ameroid placement, at a time when collateral vessel development and pacing-induced dysfunction were stable (Roth, et al. *Am J Physiol* 253:H1279–1288, 1987, and Roth, et al. *Circulation* 82:1778–1789). Conscious animals were suspended in a sling and pressures from the LV, LA and aorta, and electrocardiogram were recorded in digital format on-line (at rest and during atrial pacing at 200 bpm). Two-dimensional and M-mode images were obtained using a Hewleft Packard ultrasound imaging system. Images were obtained from a right parasternal approach at the mid-papillary muscle level and recorded on VHS tape. Images were recorded with animals in a basal state and again during right atrial pacing (HR=200 bpm). These studies were performed one day prior to gene transfer and repeated 14±1 days later. Rate-pressure products and left atrial pressures were similar in both groups before and after gene transfer, indicating similar myocardial oxygen demands and loading conditions. Echocardiographic measurements were made using standardized criteria (Sahn, et al. *Circulation* 58:1072, 1978). End-diastolic wall thickness (EDWTh) and end-systolic wall thickness (ESWTh) were measured from 5 continuous beats and averaged.

Percent wall thickening (%VVTh) was calculated |(EDWrh-ESWTh)/EDWTh|×100. Data were analyzed without knowledge of which gene the animals had received. To demonstrate reproducibility of echocardiographic measurements, animals (n=5) were imaged on two consecutive days, showing high correlation ($r^2$=0.90; p=0.005).

35±3 days after ameroid placement, well after ameroid closure, but before gene transfer, contrast echocardiographic studies were performed using the contrast material (Levovist) which was injected into the left atrium during atrial pacing (200 bpm). Studies were repeated 14±1 days after gene transfer. Peak contrast intensity was measured from the video images using a computer-based video analysis program (Color Vue II, Nova Microsonics, Indianapolis, Ind.), that provided an objective measure of video intensity. The contrast studies were analyzed without knowledge of which gene the animals had received.

At completion of the study, animals were anesthetized and midline thoracotomy performed. The brachycephalic artery was isolated, a canula inserted, and other great vessels ligated. The animals received intravenous heparin (10,000 IU) and papaverine (60 mg). Potassium chloride was given to induce diastolic cardiac arrest, and the aorta cross-clamped. Saline was delivered through the brachycephalic artery cannula (120 mmHg pressure), thereby perfusing the coronary arteries. Glutaraldehyde solution (6.25%, 0.1 M cacodylate buffer) was perfused (120 mmH pressure) until the heart was well fixed (10–15 min). The heart was then removed, the beds identified using color-coded dyes injected anterograde through the left anterior descending (LAD), left circumflex (LCx), and right coronary arteries. The ameroid was examined to confirm closure. Samples taken from the normally perfused and ischemic regions were divided into thirds and the endocardial and epicardial thirds were plastic-imbedded. Microscopic analysis to quantitate capillary number was conducted as previously described (Mathieu-Costello, et al. *Am J Physiol* 359:H204, 1990). Four 1 pm thick transverse sections were taken from each subsample (endocardium and epicardium of each region) and point-counting was used to determine capillary number per fiber number ratio at 400× magnification. Twenty to twenty-five high power fields were counted per subsample. Within each region, capillary number to fiber number rations were similar in endocardium and epicardium so the 40–50 field per region were averaged to provide the transmural capillary to fiber number ratio.

To establish that improved regional function and blood flow resulted from transgene expression, PCR and RT-PCR were used to detect transgenic FGF-5 DNA and mRNA in myocardium from animals that had received FGF-5 gene transfer. Using a sense primer to the CMV promoter [GCAGAGCTCGTTTAGTGMC] (SEQ ID NO.:1) and an antisense primer to the internal FGF-5 sequence [GAAAATGGGTAGAGATATGCT] (SEQ ID NO.:2), PCR amplified the expected 500 bp fragment. Using a sense primer to the beginning of the FGF-5 sequence [ATGAGCTTGTCCTTCCTCCTC] (SEQ ID NO.:3) and an antisense primer to the internal FGF-5 sequence [GAAAATGGGTAGAGATATGCT] (SEQ ID NO.:2), RT-PCR amplified the expected 400 bp fragment.

Finally, using a polyclonal antibody directed against FGF-5 (Kitaoka, et al. *Science* 35:3189, 1994), FGF-5 protein expression was demonstrated 48 hours as well as 14±1 days after FGF-5 gene transfer in cells and myocardium from animals that had received gene transfer with FGF-5.

The helper independent replication deficient human adenovirus 5 system constructed in Example 1 was used to prepare transgene containing vectors. The genes of interest were lacZ and FGF-5. The material injected in vivo was highly purified and contained no wild-type (replication competent) adenovirus. Thus adenoviral infection and inflammatory infiltration in the heart were minimized. By injecting the material directly into the lumen of the coronary artery by coronary catheters, it was possible to target the gene effectively. When delivered in this manner there was no transgene expression in hepatocytes, and viral RNA could not be found in the urine at any time after intracoronary injection.

Injection of the construct (4.0 ml containing about $10^{11}$ viral particles of adenovirus) was made by injecting 2.0 ml into both the left and right coronary arteries (collateral flow to the LCx bed appeared to come from both vessels). Animals were anesthetized, and arterial access acquired via the right carotid by cut-down; a 5F Cordis sheath was placed. A 5F Multipurpose (A2) coronary catheter was used to engage the coronary arteries. Closure of the LCx ameroid was confirmed by contrast injection into the left main coronary artery. The catheter tip was then placed 1 cm within the arterial lumen so that minimal material would be lost to the proximal aorta during injection. This procedure was carried out for each of the pigs.

Once gene transfer was performed, three strategies were used to establish successful incorporation and expression of the gene. (1) Some constructs included a reporter gene (lacZ); (2) myocardium from the relevant beds was sampled, and immunoblotting was performed to quantitate the presence of FGF-5; and (3) PCR was used to detect FGF-5 mRNA and DNA.

Figure 2:
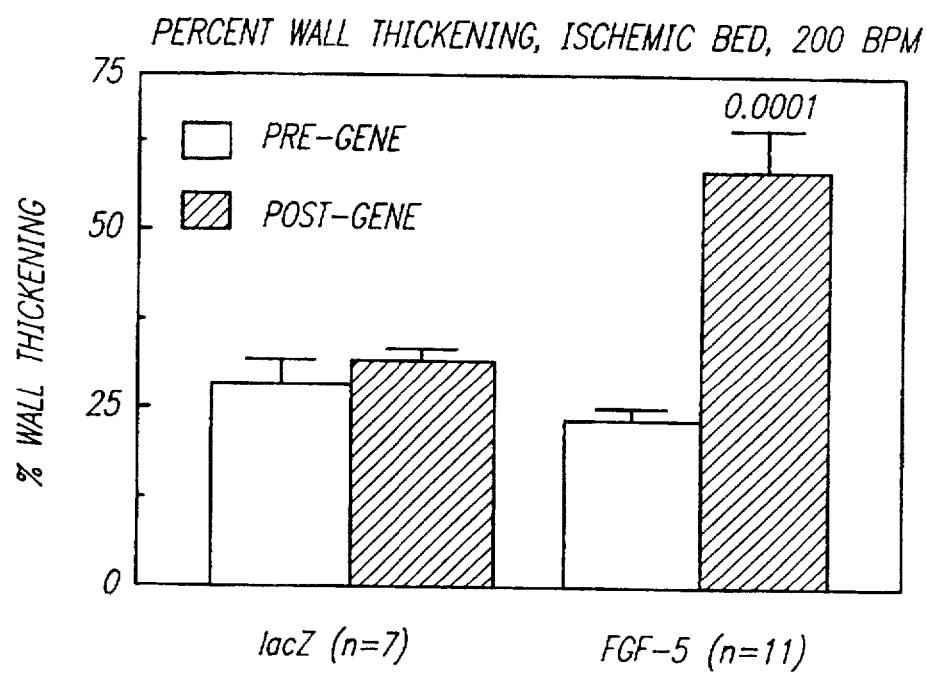
FIG. 2 shows percent wall thickening (%WTh) in the ischemic bed during right atrial pacing (HR=200 bpm), calculated by measuring end-diastolic wall thickness (EDWTh) and end-systolic wall thickness (ESVTh) before and 14±1 days after gene transfer with lacZ (control gene) and with FGF-5. Function in the ischemic bed was increased 2.6-fold after transfer with FGF-5 (p=0.0001) but unaffected by the control gene.

The regional contractile function data in FIG. 2 shows that pigs receiving lacZ showed a similar degree of pacing-induced dysfunction in the ischemic region before and 14±1 days after gene transfer. In contrast, pigs receiving FGF-5 gene transfer showed a 2.6 fold increase in wall thickening in the ischemic region during pacing ($p=0.0001$). These data demonstrate that FGF-5 gene transfer in accordance with the invention was associated with improved contraction in the ischemic region during pacing. Wall thickening in the normally perfused region (the interventricular septum) was normal during pacing and unaffected by gene transfer (% Wall Thickening: lacZ Group: Pre-gene, 56±11%, Post-gene, 51±9%; FGF-5 Group: Pre-gene, 63±7%, Post-gene, 58±5%; no differences, two-way analysis of variance). The data from the separate determinations were highly reproducible (lateral wall thickening: $r^2=0.90$; $p=0.005$). The percent decrease in function measured by transthoracic echocardiography was very similar to the percentage decrease measured by sonomicrometry during atrial pacing in the same model (Hammond, et al. *J Clin Invest* 92:2644, 1993), documenting the accuracy of echocardiography for the evaluation of ischemic dysfunction. Bars in FIG. 2 represent mean values, error bars denote 1 SE. FIGS. 4A-4C are diagrams corresponding to myocardial contrast echocardiographs. FIG. 4A illustrates acute LCx occlusion in a normal pig, in which no flow is indicated in LCx bed (black) while septum (IVS) enhances (white), confirming that the image accurately identified the LCx bed and that reduced blood flow was associated with reduced contrast enhancement. FIG. 4B illustrates the difference in contrast enhancement between IVS and LCx bed 14 days after gene transfer with lacZ, indicating different blood flows in two regions during atrial pacing (200 bpm). In FIG. 4C, contrast enhancement appears equivalent in IVS and LCx bed 14 days after gene transfer with FGF-5, indicating similar blood flows in the two regions during atrial pacing.

Figure 3:
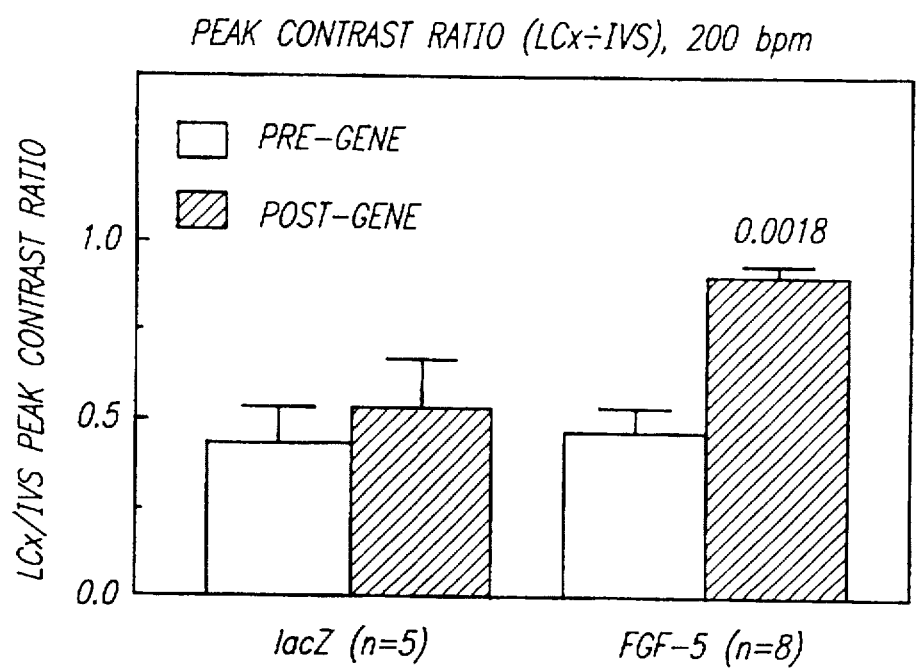
FIG. 3 shows the peak contrast ratio (a correlate of blood flow) expressed as the ratio of the peak video intensity in the ischemic region (LCx bed) divided by the peak video intensity in the interventricular septum (IVS), measured from the video images using a computer-based video analysis program during atrial pacing (200 bpm) before and 14±1 days after gene transfer with lacZ (control gene) and with FGF-5. Blood flow to the ischemic bed increased 2-fold normal after gene transfer with FGF-5 (p=0.0018), but remained 50% of normal after the control gene.

FIG. 3 summarizes computer analysis of video intensity in the two regions from all animals. In FIG. 3, data were expressed as the ratio of the peak video intensity (a correlate of myocardial blood flow) in the ischemic region (LCx bed) divided by the peak video intensity in the interventricular septum (IVS, a region receiving normal blood flow through the unoccluded left anterior descending coronary artery). Equal flows in the two regions would yield a ratio of 1.0. The ratio, prior to gene transfer, averaged 0.5, indicates substantially less flow in the LCx bed that in the septum. FIG. 3 shows that animals receiving lacZ gene transfer had a persistent blood flow deficit in the ischemic region. Animals receiving FGF-5 gene transfer showed homogeneous contrast enhancement in the two regions, indicating a 2-fold increase in myocardial blood flow improved flow in the ischemic region ($p=0.0018$, two-way analysis of variance). Bars represent mean values, error bars denote 1 SE.

Figure 5:
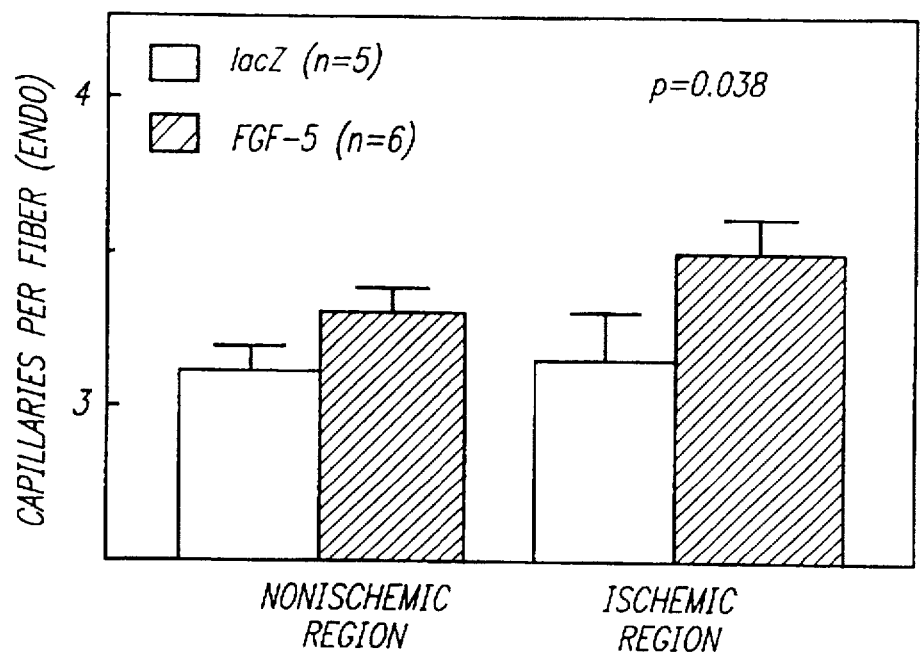
FIG. 5 shows the ratio of capillary number to fiber number quantitated by microscopic analysis in the ischemic and nonischemic regions after gene transfer with FGF-5 and with lacZ. There was increased angiogenesis after FGF-5 gene transfer (p<0.038).

The bar graph in FIG. 5 summarizes the microscopic analysis data, showing increased capillary number to fiber number ratio in the ischemic and nonischemic regions of animals that received gene transfer with FGF-5 when compared to the same regions of the hearts of animals that had received gene transfer with lacZ. Bars represent mean values from 5–6 animals in each group. Error bars denote 1 SE, p value from 2-way analysis of variance for gene effect. The analysis was performed without knowledge of treatment group.

Electropherograms upon the PCR amplification confirmed the presence of JM17-CMV-FGF-5 DNA (the expected 500 bp fragment) in the LAD and LCx beds of three pigs 14 days after gene transfer with FGF-5. Electropherogram upon the RT-PCR amplification confirmed the presence of cardiac FGF-5 mRNA (the expected 400 bp fragment) in the LAD and LCx beds 14 days after gene transfer with FGF-5, but not with lacZ. In addition, two weeks after gene transfer, myocardial samples from all five lacZ-infected animals showed substantial β-galactosidase activity on histological inspection.

Finally, immunoblots of cell medium from cultured fibroblasts with the use of the polyclonal antibodies to FGF-5 confirmed protein expression and extracellular secretion 2 days after gene transfer of FGF-5 (n=4 plates), but not after gene transfer of lacZ. Protein expression was also confirmed in myocardial samples 14±1 days after gene transfer of FGF-5 but not after gene transfer of lacZ (n=4).

We claim:

1. A method for stimulating coronary collateral vessel development in a patient, comprising delivering a replication-deficient adenovirus vector to the myocardium of the patient by intracoronary injection directly into one or both coronary arteries, said vector comprising a transgene coding for an angiogenic protein or peptide, and which expresses the transgene in the myocardium, thereby promoting coronary collateral vessel development.

2. The method of claim 1, wherein a single injection of said vector is delivered.

3. The method of claim 1, wherein about $10^7$ to about $10^{13}$ adenovirus vector particles are delivered in the injection.

4. The method of claim 1, wherein about $10^9$ to about $10^{12}$ adenovirus vector particles are delivered in the injection.

5. The method of claim 1, wherein about $10^{11}$ adenovirus vector particles are delivered in the injection.

6. The method according to claim 1, wherein said transgene is driven by a CMV promoter which is contained in the vector.

7. The method according to claim 1, wherein said transgene is driven by a ventricular myocyte-specific promoter which is contained in the vector.

8. The method according to claim 7, wherein said ventricular myocyte-specific promoter has the sequences of ventricular myosin light chain-2.

9. The method according to claim 7, wherein said ventricular myocyte-specific promoter has the sequences of myosin heavy chain promoter.

10. The method of claim 1, wherein said angiogenic protein or peptide is a fibroblast growth factor.

11. The method of claim 10, wherein said angiogenic protein is fibroblast growth factor 5.

12. The method of claim 10, wherein said angiogenic protein is acidic fibroblast growth factor.

13. The method of claim 10, wherein said angiogenic protein is basic fibroblast growth factor.

14. The method of claim 1, wherein said angiogenic protein is vascular endothelial growth factor.

15. The method of claim 1, wherein said intracoronary injection is conducted at least about 1 cm into the lumens of the left and right coronary arteries.

16. The method of claim 1, wherein said intracoronary injection is conducted at least about 1 cm into the lumens of a sapheous vein graft and/or an internal mammary artery graft in addition to a coronary artery.

17. The method of claim 1, wherein said transgene is operably linked to a tissue specific promoter which is contained in the vector whereby expression of said transgene is controlled by said promoter.

18. The method of claim 1, wherein said patient has myocardial ischemia.

19. A method for stimulating vessel development in a patient having peripheral-deficient vascular disease, comprising delivering a replication-deficient adenovirus vector to the peripheral vascular system of the patient by intrafemoral artery injection directly into one or both femoral arteries, said vector comprising a transgene coding for an angiogenic protein or peptide, and the transgene in the peripheral vascular system, thereby promoting peripheral vascular development.

20. The method of claim 19, wherein a single injection of said vector is delivered.

21. The method of claim 19, wherein about $10^9$ to about $10^{13}$ adenovirus vector particles are delivered in the injection.

22. The method of claim 19, wherein about $10^9$ to about $10^{12}$ adenovirus vector particles are delivered in the injection.

23. The method of claim 19, wherein about $10^{11}$ adenovirus vector particles are delivered in the injection.

24. The method according to claim 33, wherein said angiogenic protein or peptide is selected from the group consisting of aFGF, bFGF, FGF-5, and VEGF.

25. A method for treating heart myocardial ischemia, comprising delivering a replication-deficient adenovirus vector to the myocardium of a patient by intracoronary injection, said vector comprising a transgene coding for an angiogenic protein or peptide, and which expresses the transgene in the myocardium, thereby promoting coronary collateral vessel development.

26. The method of claim 25, wherein said intracoronary injection is directed to one or both coronary arteries.

27. The method of claim 25, wherein said intracoronary injection is directed to the left coronary artery.

28. The method of claim 26, wherein said intracoronary injection is conducted at least about 1 cm into the lumens of both coronary arteries.

29. The method of claim 28, wherein said intracoronary injection is conducted at least about 1 cm into the lumens of a saphenous vein graft or an internal mammary artery graft in addition to the left or right coronary arteries.

30. The method of claim 29, wherein said intracoronary injection is conducted at least about 1 cm into the lumens of a saphenous vein graft or an internal mammary artery graft in addition to the left coronary artery.

31. The method of claim 39, wherein said intracoronary injection is conducted at least about 1 cm into the lumens of a saphenous vein graft or an internal mammary artery graft in addition to the right coronary artery.

32. The method of claim 25, wherein said angiogenic protein or peptide is a fibroblast growth factor.

33. The method of claim 25, wherein said angiogenic protein is fibroblast growth factor 5.

34. The method of claim 25, wherein said intracoronary injection is directed to the right coronary artery.

35. The method of claim 25, wherein said intracoronary injection is conducted at least about 1 cm into the lumen of the left coronary artery.

36. The method of claim 25, wherein said intracoronary injection is conducted at least about 1 cm into the lumen of the right coronary artery.

37. The method of any one of claims 25, wherein said angiogenic protein or peptide is a vascular endothelial growth factor.

38. The method of claims 1 or 25, wherein expression of said transgene is limited to the heart.

39. The method of claim 38, wherein expression of said transgene is limited to the cardiac myocytes.

40. The method of claim 39, wherein expression of said transgene is limited to the ventricular cardiac myocytes.

41. The method of claims 10 or 32, wherein said fibroblast growth factor is selected from the group consisting of acidic fibroblast growth factor, basic fibroblast growth factor, and fibroblast growth factor 5.

* * * * *

UNITED STATES PATENT AND TRADEMARK OFFICE
CERTIFICATE OF CORRECTION

PATENT NO. : 5,792,453
DATED : August 11, 1998
INVENTOR(S) : H. Kirk HAMMOND et al.

It is certified that error appears in the above-indentified patent and that said Letters Patent is hereby corrected as shown below:

In Claim 16, line 3, please correct the spelling of "sapheous" to --saphenous--, and change "and/or" to --or--;

In Claim 19, line 7, insert --which expresses-- between "peptide, and" and "the transgene";

In Claim 21, line 1 change "$10^9$" to --$10^7$--;

In Claim 24, line 1, replace "claim 33" with --claim 19--;

In Claim 25, line 1, delete "heart";

In Claim 26, line 2, delete "one or";

In Claim 31, line 1, replace "claim 39" with --claim 29--; and

In Claim 37, replace "one of claims 25," with --one of claims 1 or 25--.

Signed and Sealed this

Seventeenth Day of April, 2001

Attest:

NICHOLAS P. GODICI

*Attesting Officer*   *Acting Director of the United States Patent and Trademark Office*

SEQUENCE LISTING ( 1 ) GENERAL INFORMATION:

( i i i ) NUMBER OF SEQUENCES: 3

-continued ( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:1:

GCAGAGCTCG TTTAGTGAAC         20

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( v ) FRAGMENT TYPE:

( v i ) ORIGINAL SOURCE:

( x i ) SEQUENCE DESCRIPTION: SEQ ID NO:2:

GAAAATGGGT AGAGATATGC T         21

( 2 ) INFORMATION FOR SEQ ID NO:3:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: NO ( v ) FRAGMENT TYPE:

( v i ) ORIGINAL SOURCE:

( x i ) SEQUENCE DESCRIPTION: SEQ ID NO:3:

ATGAGCTTGT CCTTCCTCCT C         21